(12) United States Patent
Zeng et al.

(10) Patent No.: US 12,428,414 B2
(45) Date of Patent: Sep. 30, 2025

(54) METHODS FOR PURIFYING ISAVUCONAZONIUM SULFATE

(71) Applicant: Basilea Pharmaceutica International AG, Basel (CH)

(72) Inventors: Weipeng Zeng, Basel (CH); Marco Mazzotti, Basel (CH); Lars Vicum, Basel (CH); Jeroen Cornel, Basel (CH); Markus Heubes, Basel (CH); Michael Schleimer, Basel (CH)

(73) Assignee: Basilea Pharmaceutica International AG, Basel (CH)

( * ) Notice: Subject to any disclaimer, the term of this patent is extended or adjusted under 35 U.S.C. 154(b) by 1248 days.

(21) Appl. No.: 17/260,682

(22) PCT Filed: Jul. 29, 2019

(86) PCT No.: PCT/EP2019/070385
§ 371 (c)(1),
(2) Date: Jan. 15, 2021

(87) PCT Pub. No.: WO2020/025553
PCT Pub. Date: Feb. 6, 2020

(65) Prior Publication Data
US 2021/0323959 A1    Oct. 21, 2021

(30) Foreign Application Priority Data

Aug. 1, 2018 (WO) ............... PCT/CN2018/097881
Jun. 6, 2019 (WO) ............... PCT/CN2019/090347

(51) Int. Cl.
*C07D 417/14*    (2006.01)

(52) U.S. Cl.
CPC ........ *C07D 417/14* (2013.01); *C07B 2200/13* (2013.01)

(58) Field of Classification Search
CPC .................. C07D 417/14; C07B 2200/13
See application file for complete search history.

(56) References Cited

FOREIGN PATENT DOCUMENTS

| CN | 106467534 A | 3/2017 |
|---|---|---|
| CN | 106543165 A | 3/2017 |

(Continued)

OTHER PUBLICATIONS

The International Search Report and Written Opinion, mailed Apr. 15, 2019 for the priority application PCT/CN2018/097881.

(Continued)

*Primary Examiner* — Andrew D Kosar
*Assistant Examiner* — John D Mcanany (57) ABSTRACT

The invention provides methods for purifying isavuconazonium sulfate comprising the steps of —(a) providing a mixture comprising the sulfate salt of the compound of formula (I) and an aliphatic alcohol, wherein the pH of the mixture is in the range of about pH 1 to about pH 6; —(b) allowing a first portion of the sulfate salt of the compound of formula (I) to crystalize from the mixture; and —(c) adding an aprotic organic solvent to the mixture and allowing an additional portion of the sulfate salt of the compound of formula (I) to precipitate from the mixture.

(Continued)

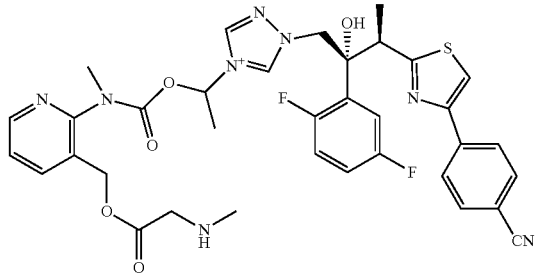

(I)

29 Claims, 1 Drawing Sheet

(56) References Cited

FOREIGN PATENT DOCUMENTS

| CN | 106565699 A | 4/2017 |
|----|-------------|--------|
| CN | 106619541 A | 5/2017 |
| CN | 106749221 A | 5/2017 |
| CN | 106749222 A | 5/2017 |
| CN | 106916152 A | 7/2017 |
| CN | 107445951 A | 12/2017 |
| CN | 107661298 A | 2/2018 |
| CN | 107778306 A | 3/2018 |
| CN | 107982221 A | 5/2018 |
| CN | 109206421 A | 1/2019 |
| IN | 201621035182 A | 10/2019 |
| WO | 2015/150947 A1 | 10/2015 |
| WO | 2016/016766 A2 | 2/2016 |
| WO | 2016/055918 A1 | 4/2016 |

OTHER PUBLICATIONS

The International Search Report and Written Opinion, mailed Oct. 24, 2019 for the corresponding PCT application PCT/EP2019/070385.

The English translation of the Chinese Office Action, mailed on Sep. 21, 2023, in the related Chinese Appl. No. 201980047270.9.

Liu et al., Comprehensive Chemical Experiments I, 1st edition, pp. 29-31, Aug. 31, 2016.

METHODS FOR PURIFYING ISAVUCONAZONIUM SULFATE

This application is a National Stage Application of PCT/EP2019/070385 filed Jul. 29, 2019, which claims priority from PCT Patent Application No. PCT/CN2018/097881, filed on Aug. 1, 2018 and PCT Patent Application No. PCT/CN2019/090347 filed Jun. 6, 2019. The priority of said PCT and prior-filed two PCT Patent Applications are claimed. Each of the prior mentioned applications is hereby incorporated by reference herein in its entirety.

The present invention provides methods for purifying isavuconazonium sulfate and epimers thereof.

Isavuconazonium sulfate is a prodrug of the broad spectrum azole antifungal agent isavuconazole. It is being commercialised for the treatment of aspergillosis and mucormycosis and is available as oral and intravenous formulations. Isavuconazonium salts are described in WO2001/32652 and a method for preparing isavuconazonium hydrochloride is given in Example 7. However, due to its sensitivity to moisture, isavuconazonium salts such as the commercial product isavuconazonium sulfate, are difficult to purify from crude material in high yield.

Attempts have been made to purify isavuconazonium sulfate by crystallisation. For example, CN106565699 describes methods of preparing a crystal form of isavuconazonium sulfate. The method involves step 1: dissolving isavuconazole hydrochloride in water, adjusting the pH to neutral using a base at a low temperature, adding an organic solvent A for extraction, drying and concentrating and then dissolving in an organic solvent B, adding concentrated sulfuric acid and hydrogen peroxide at a low temperature, stirring, and concentrating; step 2: adding the abovementioned concentrate to an organic solvent C, heating to dissolve, stirring and cooling to crystallize, and performing suction filtration to obtain a crystal. This method is however not suitable for commercial scale-up. In particular the use of hydrogen peroxide leads to significant degradation of the product.

CN106467534 also describes methods of preparing a crystal form of isavuconazonium sulfate. The method involves (a) dissolving the crude isavuconazonium sulphate product in a mixed solution of water, an organic solvent A and an organic solvent B, (b) dropwise adding an organic solvent C to the isavuconazonium sulphate solution obtained in step (a); and (c) performing stirring crystallization and separation to obtain said isavuconazonium sulphate compound, wherein the organic solvent A refers to R1-O—CH2-CH2OH; the organic solvent B refers to R2-C(=O)—R3 and/or tetrahydrofuran; and the organic solvent C refers to R4-C(=O)O—R5; R1, R2, R3, R4 and R5 being independently selected from C1-3 alkyl.

However, as shown in the Comparative Examples below we have found that the method described in CN106467534 results in low yield when the crude material is of lower purity. In addition when starting from high purity material CN106467534 produces a isavuconazonium sulfate product which is highly enriched for one of the two epimers, whereas the approved commercial product has a molar epimer ratio of 1.2:1 to 1:1.2.

The two epimers of isavuconazonium are depicted here:

The present invention provides new procedures for the purification of isavuconazonium sulfate, referred to herein as the sulfate salt of the compound of formula I.

In a first aspect the invention provides a method for purifying the sulfate salt of the compound of formula I (I)

comprising the steps of
(a) providing a mixture comprising the sulfate salt of the compound of formula I and an aliphatic alcohol, wherein the pH of the mixture is in the range of about pH 1 to about pH 6;
(b) allowing a first portion of the sulfate salt of the compound of formula I to crystallize from the mixture; and
(c) adding an aprotic organic solvent to the mixture and allowing an additional portion of the sulfate salt of the compound of formula I to precipitate from the mixture.

The epimers of the sulfate salt of the compound of formula I are defined herein by reference to their retention times. Epimer A is the first epimer to elute from a chiral HPLC column functionalized with phenylcarbamated β-cyclodextrin in which the mobile phase is a mixture of triethylammonium acetate and acetonitrile in proportions 40:60 at pH 6.5.

Generally the mixture provided in step (a) comprises a mixture of epimer A and epimer B of the sulfate salt of the compound of formula I, usually in similar amounts. The portions obtained from step (b) and step (c) contain different proportions of epimer A and epimer B. Step (b) selectively crystallizes epimer B, whilst step (c) is effective for precipitating epimer A remaining in the solution. Thus, in the absence of step (c) the resulting crystalline form from step (b) will tend to be of lower yield because a large portion of epimer A will still be in solution. In addition, for this reason the ratio of epimers will usually not correspond to the ratio required for commercialization, namely a ratio of 1.2:1 to 1:1.2. When step (c) is included, a larger proportion of epimer A precipitates, which may allow a resulting ratio of epimer A to epimer B within the limits required for the commercial product.

The molar ratio of epimer B to epimer A in the portion of the sulfate salt of the compound of formula I obtained from step (b) is generally greater than 1:1, e.g. at least 1.3:1, e.g. at least 1.5:1, e.g. at least 2:1, e.g. at least 5:1, e.g. in the range of 1.3:1 to 100:1, e.g. in the range of 1.5:1 to 50:1 e.g. in the range of 2:1 to 20:1, e.g. in the range of 5:1 to 20:1.

The molar ratio of epimer A to epimer B in the portion of the sulfate salt of the compound of formula I obtained from step (c) is generally greater than 1:1, e.g. at least 1.3:1, e.g. at least 1.5:1, e.g. at least 2:1, e.g. at least 5:1, e.g. in the range of 1.3:1 to 100:1, e.g. in the range of 1.5:1 to 50:1 e.g. in the range of 2:1 to 20:1, e.g. in the range of 5:1 to 20:1.

The molar ratio of epimer A to epimer B in the combined portions of the sulfate salt of the compound of formula I from step (b) and step (c) taken together may be 2:1 to 1:2, e.g. about 1.2:1 to about 1.1.2.

The mixture provided in step (a) may be prepared from the solid crude product obtained from the synthesis of the sulfate salt of the compound of formula I, which may be synthesized by the person skilled in the art according to known procedures. In one embodiment the precursor to the compound of formula I is the sulfate salt of the Boc protected analogue of the compound of formula I (compound 6 as depicted in CN106916152A), which may be deprotected using sulfuric acid using a suitable solvent, e.g. ethylacetate, e.g. at a temperature in the range of 20° C. to 25° C., to give the sulfate salt of the compound of formula I. This may be allowed to precipitate, e.g. in water, to give solid crude product, which may optionally be washed, e.g. with a protic organic solvent such as isopropanol.

Solid crude product will contain impurities formed during the synthesis of the sulfate salt of the compound of formula I. The purity of the sulfate salt of the compound of formula I in the solid crude product which may be used in step (a) is usually e.g. (before or after washing) at least 80% (i.e. the weight amount of the sulfate salt of the compound of formula I relative to the weight amount of impurities), e.g. in the range of 80% to 100%, e.g. in the range of 90% to 100%, e.g. in the range of 90% to 99%, e.g. in the range of 90% to 98%, e.g. in the range of 90% to 97%, e.g. in the range of 90% to 96%, e.g. in the range of 90% to 95%, e.g. in the range of 93% to 100%, e.g. in the range of 93% to 98%. In other embodiments the purity of the sulfate salt of the compound of formula I in the solid crude product which may be used in step (a) may be no more than 98%, e.g. no more than 97%, e.g. no more than 96%, no more than 95%.

The mixture of step (a) may be provided by dissolving the solid crude product of the sulfate salt of the compound of formula I in the aliphatic alcohol. An aliphatic moiety is a non-aromatic hydrocarbon moiety in which the constituent carbon atoms can be straight-chain, branched chain, or cyclic. Aliphatic alcohols according to the invention contain one or two OH groups, providing that when there are two OH groups there are three to six carbon atoms in the aliphatic moiety. The aliphatic alcohol may be C2-C10alkyl-OH or C3-C10cycloalkyl-OH (e.g. cyclopentanol, cyclohexanol, cycloheptanol) or a mixture thereof, in particular C2-C10alkyl-OH. In one embodiment the aliphatic alcohol is an aliphatic alcohol selected from ethanol, propanol (including any isomer thereof e.g. propan-1-ol, isopropanol), butanol (including any isomer thereof, e.g. n-butan-1-ol, n-butan-2-ol, t-butan-1-ol, t-butan-2-ol), and pentanol (including any isomer thereof) or a mixture thereof. In another embodiment the aliphatic alcohol is propanol or ethanol or a mixture thereof. In another embodiment the aliphatic alcohol is ethanol or n-butanol. In another embodiment the aliphatic alcohol is ethanol.

The v/w ratio (i.e. milliliters:grams) of the aliphatic alcohol to the sulfate salt of the compound of formula I may be up to 100:1 e.g. up to 75:1, e.g. up to 40:1, e.g. up to 20:1, e.g. up to 10:1, e.g. up to 8:1, e.g. up to 6:1, e.g. up to 5:1, e.g. at least 1:1, e.g. at least 2:1, e.g. in the range of 1:1 to 100:1, e.g. in the range of 1:1 to 75:1, e.g. in the range of 1:1 to 40:1, e.g. in the range of 1:1 to 20:1 e.g. in the range of 1:1 to 10:1, e.g. in the range of 2:1 to 10:1, e.g. in the range of 2:1 to 8:1, e.g. in the range of 2:1 to 6:1, e.g. in the range of 3:1 to 5:1, e.g. about 4:1. For example the v/w ratio of ethanol to the sulfate salt of the compound of formula I may be up to 100:1, e.g. up to 75:1, e.g. up to 40:1, e.g. up to 20:1, e.g. up to 10:1, e.g. up to 8:1, e.g. up to 6:1, e.g. up to 5:1, e.g. at least 1:1, e.g. at least 2:1, e.g. in the range of 1:1 to 100:1, e.g. in the range of 1:1 to 75:1, e.g. in the range of 1:1 to 40:1, e.g. in the range of 1:1 to 20:1 e.g. in the range of 1:1 to 10:1, e.g. in the range of 2:1 to 10:1, e.g. in the range of 2:1 to 8:1, e.g. in the range of 2:1 to 6:1, e.g. in the range of 3:1 to 5:1, e.g. about 4:1.

Optionally the mixture in step (a) comprises water in addition to the aliphatic alcohol. The v/v ratio of the aliphatic alcohol to water may be up to 500:1, e.g. in the range of 1:1 to 50:1, e.g. in the range of 5:1 to 50:1, e.g. in the range of 5:1 to 30:1, e.g. in the range of 10:1 to 30:1, e.g. in the range of 15:1 to 25:1, e.g. about 20:1. For example, the v/v ratio of ethanol to water may be up to 500:1, e.g. in the range of 1:1 to 50:1, e.g. in the range of 5:1 to 50:1, e.g. in the range of 5:1 to 30:1, e.g. in the range of 10:1 to 30:1, e.g. in the range of 15:1 to 25:1, e.g. about 20:1.

In one embodiment the mixture of step (a) is provided by obtaining solid crude product comprising the sulfate salt of the compound of formula I and dissolving the solid crude product in the aliphatic alcohol and optionally water.

Dissolution of solid crude product in the aliphatic alcohol and optionally water may result in a pH which is lower than that desired due to the presence of excess sulfuric acid. When adjusting the pH it will usually be preferable to avoid the use of inorganic bases as they may lead to decomposition of the product. Alternative ways of adjusting, e.g. increasing, the pH include the use of anion exchange resins such as weak base anion exchange resins, which are commercially available, e.g. from Amberlite®. In one embodiment the pH of the mixture in step (a) is provided to be about pH 3 to about pH 6, e.g. about pH 3.8 to about pH 6. in another embodiment the pH is provided to be about pH 3 to about pH 5. In another embodiment the pH is provided to be about pH 1 to about pH 5. In another embodiment the pH is provided to be about pH 3 to about pH 4.5. In another embodiment the pH is provided to be about pH 3.8 to about pH 4.5. In another embodiment the pH is provided to be about 4. Generally the pH is increased to a value such that the mixture does not turn into an oil, but is not too high such that the sulfate salt of the compound of formula I becomes too soluble.

Generally solid crude product will be dissolved in the aliphatic alcohol (and optionally water) at a suitable temperature which is high enough to achieve dissolution, but not too high such that the compound of formula I decomposes, e.g. by hydrolysis. For example the dissolution temperature may be in the range of −70° C. to 50° C., e.g. in the range of 0° C. to 40° C., e.g. in the range of 15° C. to 30° C., e.g. in the range of 20° C. to 25° C., e.g. at least −70° C., e.g. at least 0° C., e.g. at least 15° C., e.g. up to 50° C., e.g. up to 40° C., e.g. up to 30° C., e.g. up to 25° C. The mixture may be allowed to remain at these temperatures for up to 48 hours, e.g. up to 30 hours, e.g. up to 24 hours, e.g. in the range of 1 to 48 hours, e.g. in the range of 5 to 30 hours, e.g. in the range of 12 to 24 hours, and may be stirred during this period.

Step (b) may comprise allowing a first portion of the sulfate salt of the compound of formula I to crystalize from the mixture by cooling the mixture. For example, the mixture may be cooled from the starting temperature (e.g. the dissolution temperature) to a temperature in the range of −25° C. to 20° C. (e.g. at least −25° C., e.g. up to 20° C.), e.g. in the range of −15° C. to 20° C. (e.g. at least −15° C., e.g. up to 20° C.), e.g. in the range of 5° C. to 20° C. (e.g. at least 5° C., e.g. up to 20° C.), e.g. to a temperature in the range of 5° C. to 15° C. (e.g. at least 5° C., e.g. up to 15° C.), e.g. to a temperature of about 10° C. The starting temperature (e.g. the usually the dissolution temperature) may be a temperature in the range of 5° C. to 40° C. (e.g. at least 5° C., e.g. up to 40° C.), e.g. in the range of 20° C. to 40° C. (e.g. at least 20° C., e.g. up to 40° C.), e.g. in the range of 20° C. to 30° C. (e.g. at least 20° C., e.g. up to 30° C.). The period during which the mixture is cooled may be for example 10 minutes to 48 hours, e.g. in the range of 5 to 15 hours, e.g. in the range of 8 to 12 hours, bearing in mind that prolonged periods at higher temperatures can lead to decomposition.

Examples of rates of cooling which may be used are for example not more than 3° C. per hour, e.g. not more than 2° C., e.g. not more than 1.5° C. per hour, e.g. not more than 1° C. per hour, e.g. in the range of 0.2 to 3° C. per hour, e.g. in the range of 0.5 to 1.5° C. per hour, e.g. about 1° C. per hour.

In step (b) the mixture may be allowed to stand for a suitable period, e.g. up to 10 days, e.g. in the range of 1 to 10 days, at a temperature in the range of −10° C. to 20° C. (e.g. at least −10° C., e.g. up to 20° C.), e.g. in the range of 0° C. to 15° C. (e.g. at least 0° C., e.g. up to 15° C.), e.g. about 10° C. Longer standing periods, e.g. at least 3 days, e.g. in the range of 4 to 10 days, e.g. in the range of 4 to 5 days, may allow an increase in yield, whilst avoiding oily products. The period during which the mixture is allowed to stand may be reduced by adding seed crystals.

In step (c) the aprotic organic solvent may be C4-C10alkyl, or C4-C10alkenyl or a mixture thereof. Specific examples include hexane and heptane or a mixture thereof, such as n-hexane or n-heptane or a mixture thereof. In one embodiment the aprotic solvent is n-heptane. Other specific examples include hexene and heptene, such as 1-hexene or 1-heptene. In another embodiment the aprotic solvent is 1-hexene.

The volume of aprotic organic solvent used in step (c) may be up to 8 times, e.g. up to 6 times, e.g. up to 4 times, e.g. at least 0.05 times, e.g. at least 0.1 times, e.g. at least 0.5 times, e.g. at least 1 times, e.g. at least 3 times the volume of the mixture in step (a), e.g. in the range of 0.05 to 8 times the volume of the mixture in step (a), e.g. in the range of 0.1 to 8 times, e.g. in the range of 0.5 to 6 times, e.g. in the range of 1 to 6 times, e.g. in the range of 3 to 5 times the volume of the mixture in step (a).

The aprotic organic solvent may be added to the mixture over a suitable period e.g. in the range of 10 minutes to 48 hours, e.g. in the range of 1 to 30 hours, e.g. in the range of 2 to 12 hours. The temperature during this period may be in the range of −10° C. to 20° C. (e.g. at least −10° C., e.g. up to 20° C.), e.g. in the range of 0° C. to 15° C. (e.g. at least 0° C., e.g. up to 15° C.), e.g. about 10° C. The mixture may be stirred during this period.

Following addition of the aprotic solvent the mixture may be allowed to stand for a suitable period of time, e.g. up to 5 days, e.g. in the range of 1 hour to 5 days, e.g. at a temperature in the range of −10° C. to 20° C. (e.g. at least −10° C., e.g. up to 20° C.), e.g. in the range of 0° C. to 15° C. (e.g. at least 0° C., e.g. up to 15° C.), e.g. about 10° C. The product may be dried.

Step (a) may comprise providing a mixture comprising the sulfate salt of the compound of formula I and ethanol and optionally water, and step (c) may comprise adding propanol (including any isomer thereof e.g. propan-1-ol, isopropanol) and/or butanol (including any isomer thereof, e.g. n-butan-1-ol, n-butan-2-ol, t-butan-1-ol, t-butan-2-ol), preferably isopropanol, and an aprotic organic solvent selected from hexane and heptane and a mixture thereof, preferably n-heptane, to the mixture and allowing an additional portion of the sulfate salt of the compound of formula I to precipitate from the mixture. The propanol and/or butanol may be added to the mixture prior to the aprotic organic solvent and following addition of the propanol and/or butanol the mixture may be allowed to stand prior to adding the aprotic organic solvent, e.g. to allow a portion of the sulfate salt of the compound of formula I to precipitate from the mixture prior to adding the aprotic solvent.

According to an embodiment, the invention provides a method for purifying the sulfate salt of the compound of formula I comprising the steps of:
  (a) providing a mixture comprising the sulfate salt of the compound of formula I and ethanol and optionally water, wherein the pH of the mixture is in the range of about pH 1 to about pH 6;
  (b) allowing a first portion of the sulfate salt of the compound of formula I to crystalize from the mixture;
  (c1) adding propanol and/or butanol to the mixture and allowing an additional portion of the sulfate salt of the compound of formula I to precipitate from the mixture; and
  (c2) adding hexene, heptene, hexane or heptane or a mixture thereof to the mixture and allowing a further additional portion of the sulfate salt of the compound of formula I to precipitate from the mixture.

The propanol and/or butanol may be added to the mixture over a period in the range of 10 minutes to 48 hours, e.g. in the range of 1 to 30 hours, e.g. in the range of 2 to 24 hours. The temperature during this period may be in the range of −10° C. to 20° C. (e.g. at least −10° C., e.g. up to 20° C.), e.g. in the range of 0° C. to 15° C. (e.g. at least 0° C., e.g. up to 15° C.), e.g. about 10° C. The mixture may be stirred during this period. Following additional of propanol and/or butanol the mixture may be allowed to stand for a suitable period of time prior to adding the aprotic solvent, e.g. up to 5 days, e.g. 1 hour to 5 days, e.g. at a temperature in the range of −10° C. to 20° C. (e.g. at least −10° C., e.g. up to 20° C.), e.g. in the range of 5° C. to 15° C. (e.g. at least 0° C., e.g. up to 15° C.), e.g. about 10° C.

The volume of propanol and/or butanol may be may be up to 8 times, e.g. up to 6 times, e.g. up to 5 times the volume of the mixture in step (a), e.g. at least 0.05 times, e.g. at least 0.1 times, e.g. at least 1 times, e.g. at least 4 times, e.g. in the range of 0.05 to 8 times, e.g. in the range of 0.1 to 6 times, e.g. in the range 1 to 6 times, e.g. in the range of 4 to 6 times the volume of the mixture in step (a).

The v/v ratio of the aprotic organic solvent to propanol and/or butanol may be e.g. 1:10 to 10:1, e.g. 1:5 to 5:1, e.g. 1:2 to 2:1.

According to an embodiment, the invention provides a method for purifying the sulfate salt of the compound of formula I comprising the steps of
- (a) providing a mixture comprising the sulfate salt of the compound of formula I and an aliphatic alcohol, wherein the aliphatic alcohol is C2-C10alkyl-OH or C3-C10cycloalkyl-OH or a mixture thereof, wherein the v/w ratio of the aliphatic alcohol to the sulfate salt of the compound of formula I is in the range of 1:1 to 100:1 (e.g. 1:1 to 10:1), and wherein the pH of the mixture is in the range of about pH 3 to about pH 5;
- (b) allowing a first portion of the sulfate salt of the compound of formula I to crystalize from the mixture; and
- (c) adding an aprotic organic solvent to the mixture, wherein the aprotic organic solvent is C4-C10alkyl, or C4-C10alkenyl or a mixture thereof, wherein the volume of aprotic organic solvent used in step (c) is in the range of 0.05 to 8 times the volume of the mixture in step (a), and allowing an additional portion of the sulfate salt of the compound of formula I to precipitate from the mixture.

According to an embodiment, the invention provides a method for purifying the sulfate salt of the compound of formula I comprising the steps of
- (a) providing a mixture comprising the sulfate salt of the compound of formula I and an aliphatic alcohol, wherein the aliphatic alcohol is ethanol, propanol, butanol or pentanol or a mixture thereof, wherein the v/w ratio of the aliphatic alcohol to the sulfate salt of the compound of formula I is in the range of 1:1 to 100:1 and wherein the pH of the mixture is in the range of about pH 3 to about pH 5;
- (b) allowing a first portion of the sulfate salt of the compound of formula I to crystalize from the mixture; and
- (c) adding an aprotic organic solvent to the mixture, wherein the aprotic organic solvent is hexane or heptane or a mixture thereof, wherein the volume of aprotic organic solvent is in the range of 0.5 to 6 times the volume of the mixture in step (a), and allowing an additional portion of the sulfate salt of the compound of formula I to precipitate from the mixture.

According to an embodiment, the invention provides a method for purifying the sulfate salt of the compound of formula I comprising the steps of
- (a) providing a mixture comprising the sulfate salt of the compound of formula I and an aliphatic alcohol, wherein the aliphatic alcohol is ethanol, propanol, butanol or pentanol or a mixture thereof, wherein the v/w ratio of the aliphatic alcohol to the sulfate salt of the compound of formula I is in the range of 2:1 to 6:1, and wherein the pH of the mixture is in the range of about pH 3 to about pH 5;
- (b) allowing a first portion of the sulfate salt of the compound of formula I to crystalize from the mixture; and
- (c) adding an aprotic organic solvent to the mixture, wherein the aprotic organic solvent is hexane or heptane or a mixture thereof, wherein the volume of aprotic organic solvent is in the range of 1 to 6 times the volume of the mixture in step (a), and allowing an additional portion of the sulfate salt of the compound of formula I to precipitate from the mixture.

According to an embodiment, the invention provides a method for purifying the sulfate salt of the compound of formula I comprising the steps of
- (a) providing a mixture comprising the sulfate salt of the compound of formula I, water and ethanol, wherein the v/w ratio of the ethanol to the sulfate salt of the compound of formula I is in the range of 2:1 to 6:1, wherein the v/v ratio of ethanol to water is 15:1 to 25:1, and wherein the pH of the mixture is in the range of about pH 3 to about pH 5;
- (b) allowing a first portion of the sulfate salt of the compound of formula I to crystalize from the mixture;
- (c1) adding propanol and/or butanol to the mixture, wherein the volume of propanol and/or butanol. is 1 to 6 times the volume of the mixture in step (a) and allowing an additional portion of the sulfate salt of the compound of formula I to precipitate from the mixture; and
- (c2) adding an aprotic organic solvent to the mixture, wherein the aprotic organic solvent is hexane or heptane or a mixture thereof, wherein the volume of aprotic organic solvent is in the range of 1 to 6 times the volume of the mixture in step (a), and allowing a further additional portion of the sulfate salt of the compound of formula I to precipitate from the mixture.

According to an embodiment, the invention provides a method for purifying the sulfate salt of the compound of formula I comprising the steps of
- (a) providing a mixture comprising the sulfate salt of the compound of formula I, water and ethanol, wherein the v/w ratio of the ethanol to the sulfate salt of the compound of formula I is in the range of 2:1 to 6:1, wherein the v/v ratio of ethanol to water is 15:1 to 25:1, and wherein the pH of the mixture is in the range of about pH 3 to about pH 5;
- (b) cooling the mixture and allowing a first portion of the sulfate salt of the compound of formula I to crystalize from the mixture, wherein the rate of cooling is not more than 3° C. per hour;
- (c1) adding propanol and/or butanol to the mixture, wherein the volume of propanol and/or butanol is 1 to 6 times the volume of the mixture in step (a) and allowing an additional portion of the sulfate salt of the compound of formula I to precipitate from the mixture; and
- (c2) adding an aprotic organic solvent to the mixture, wherein the aprotic organic solvent is hexane or heptane or a mixture thereof, wherein the volume of aprotic organic solvent is in the range of 1 to 6 times the volume of the mixture in step (a), and allowing a further additional portion of the sulfate salt of the compound of formula I to precipitate from the mixture; and wherein the molar ratio of the epimers in the combined portions of the sulfate salt of the compound of formula I from step (b) and steps (c1) and (c2) taken together is in the range of 1:2 to 2:1.

In a further aspect the invention provides a method for preparing epimer B of the sulfate salt of the compound of formula I in crystalline form, wherein epimer B is the second epimer of the epimers to elute from a chiral HPLC column functionalized with phenylcarbamated β-cyclodextrin in which the mobile phase is a mixture of triethylammonium acetate and acetonitrile in proportions 40:60 at pH 6.5, comprising the steps of (a) providing a mixture comprising the sulfate salt of the compound of formula I and an aliphatic alcohol, wherein the pH of the mixture is in the range of about pH 1 to about pH 6; and
(b) allowing epimer B to crystalize from the mixture.

The above description of steps (a) and (b) in relation to the first aspect of the invention also apply to steps (a) and (b) in this aspect of the invention where possible.

In a further aspect the invention provides a method for preparing epimer A of the sulfate salt of the compound of formula I in solid form, wherein epimer A is the first epimer of the epimers to elute from a chiral HPLC column functionalized with phenylcarbamated β-cyclodextrin in which the mobile phase is a mixture of triethylammonium acetate and acetonitrile in proportions 40:60 at pH 6.5, comprising the step of (c) adding an aprotic organic solvent to a mixture comprising the sulfate salt of epimer A and an aliphatic alcohol, wherein the pH of the mixture is in the range of about pH 1 to about pH 6; and allowing the sulfate salt of epimer A to precipitate from the mixture; wherein the molar amount of epimer A in the precipitate from step (c) is greater than the molar amount of epimer B.

The above description of step (c) (including the description of step (c) as steps (c1) and (c2)) in relation to the first aspect of the invention also apply to step (c) in this aspect of the invention where possible.

In a further aspect the invention provides a method for preparing a pharmaceutical composition comprising formulating the sulfate salt of the compound of formula I with one or more pharmaceutical excipients, wherein the sulfate salt of the compound of formula I has been purified by a method as described herein.

In a further aspect the invention provides a pharmaceutical composition comprising the sulfate salt of the compound of formula I and one or more pharmaceutical excipients, wherein the sulfate salt of the compound of formula I has been purified by a method as defined as described herein.

Pharmaceutical compositions comprising the sulfate salt of the compound of formula I may be prepared according to the common general knowledge of the person skilled in the art using routinely available pharmaceutical excipients. The pharmaceutical formulation may be a powder for injection or a capsule for oral administration. For example, isavuconazonium sulfate is commercially available as a lyophilised powder for intravenous administration, containing the excipients mannitol and sulfuric acid for pH adjustment and as a capsule for oral administration containing the excipients trimagnesium dicitrate, microcrystalline cellulose, talc, colloidal silica dioxide and stearic acid.

The sulfate salt of the compound of formula I purified as described herein may be formulated directly into a pharmaceutical composition or may undergo further processing steps before being formulated into a pharmaceutical composition. For example it may be re-precipitated e.g. to produce an amorphous form, e.g. as used in the approved formulation for oral administration. For example it may be dissolved in a suitable solvent and lyophilised, e.g. as used in the approved formulation for injection.

Alkyl and alkenyl groups may be linear or branched. The term "about" indicates a variation of +/−5% of the given value, preferably 2%, more preferably 1%. All ranges mentioned include the starting point and the end point of the specified range. All aspects and embodiments of the invention described herein may be combined in any combination where possible.

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Particular embodiments of the invention are described in the following Examples, which serve to illustrate the invention in more detail and should not be construed as limiting the invention in any way.

EXAMPLES

Example 1

30 g of the crude sulfate salt of the compound of formula I, HPLC purity 93.7%, was dissolved in a mixture of 90 mL ethanol and 10 mL water, the pH value of the solution was 3.5. Then the resulting solution was cooled to −20° C. from 10° C. (−1° C. per hour). The mixture was stirred at −20° C. over 16 hours and then warmed to 5° C. The mixture was then stirred at 5° C. over 16 hours. After filtration and drying 5 g of the sulfate salt of the compound of formula I was obtained as white crystalline Form I with 98.5% HPLC purity in 16.6% yield (epimer ratio not determined).

Example 2

75 g of the crude sulfate salt of the compound of formula I, HPLC purity 94.8%, was dissolved in a mixture of 225 mL ethanol and 25 mL water, pH 2.8, and stirred at 8° C. over 2 days. After filtration and drying 18 g of the sulfate salt of the compound of formula I was obtained as white crystalline Form I with 98% HPLC purity in 24% yield (epimer ratio not determined).

Example 3

1 g of the crude sulfate salt of the compound of formula I, HPLC purity 85.2%, was dissolved in 3.6 mL ethanol and 0.4 mL water, the pH value was 5.1. This solution was cooled to 19° C. from 25° C. and 0.55 g of a white precipitate of the sulfate salt of the compound of formula I was formed with 92% HPLC purity in 55% yield. XRPD analysis indicated that the sulfate salt of the compound of formula I was obtained as crystalline Form II (epimer ratio not determined).

Example 4

0.9 g of the crude sulfate salt of the compound of formula I, HPLC purity 85.2%, was dissolved in 4.5 mL ethanol and 0.5 mL water and the pH value was adjusted to 3.7 with concentrated sulfuric acid. The solution was cooled to −10° C. from 20° C. over 15 hours and a precipitate of the sulfate salt of the compound of formula I was formed. The precipitate was filtered and dried to give 0.36 g crystalline Form II with 98% HPLC purity in 36% yield (epimer ratio not determined).

Example 5

6 g of the crude sulfate salt of the compound of formula I, HPLC purity 85.2%, was dissolved in 36 mL ethanol and 4 mL water, the pH value was 4.2. This solution was then cooled to −10° C. from 20° C. over 15 hours and a precipitate of the sulfate salt of the compound of formula I was formed. The precipitate was filtered and dried to give 0.36 g crystalline Form II in 35% yield (epimer ratio not determined).

Example 6

101 g of the crude sulfate salt of the compound of formula I, HPLC purity 95.6%, was dissolved in 400 mL ethanol and 20 mL water, the pH value was 4.0. 1.0 g of crystalline Form I was added as seed. The mixture was then stirred over 16 hours at 20-25° C., cooled to 10° C. over 10 hours and was allowed to stand for over 5 days at a 0-10° C. During this time a precipitate formed giving 35% yield and an epimer A to epimer B ratio of 1:11. 1.5 L of isopropanol was then added over 21 hours, and 2 L of n-heptane was charged over 12 hours. After filtration and drying, 52 g of the sulfate salt of the compound of formula I as crystalline Form I with 97.4% purity was obtained, giving a total 71.7% yield and an epimer A to epimer B ratio of 1:1.18.

Example 7

10 g of the crude sulfate salt of the compound of formula I, HPLC purity 95.6% was dissolved in 40 mL ethanol and 2 mL water, the pH value was 4.0. 0.05 g of crystalline Form I was added as seed.

The mixture was then stirred over 16 hours at 20-25° C., cooled to 10° C. over 10 hours and was allowed to stand for over 5 days at 10° C. After filtration and drying, 2.2 g of the sulfate salt of the compound of formula I as crystalline Form I with 99.0% purity was obtained in 35% yield with an epimer A to epimer B ratio of 1:10.8.

Example 8

2.8 g of crude sulfate salt of the compound of formula I (BAL0008557-002), HPLC purity 94.9% was dissolved in 100 mL cyclohexanol and 5 mL water, the pH value was adjusted to 4.1. 0.03 g of crystalline form I was added as seed. The mixture was then stirred over 16 hours at 20-25° C., cooled to 5-10° C. over 10 hours and was allowed to stand for over 5 days at SoC. 75 mL of isopropanol was then added over 2 hours, and 100 mL of n-heptane was charged over 3 hours. After filtration and drying, 0.71 g of the sulfate salt of the compound of formula I as crystalline Form I with 98.1% purity was obtained, giving a total 40.5% yield and an epimer A to epimer B ratio of 1.89.

Example 9

2 g of crude sulfate salt of the compound of formula I (BAL0008557-002), HPLC purity 94.9% was dissolved in 100 mL n-butanol and 5 mL water, the pH value was adjusted to 4.0. 0.02 g of crystalline form I was added as seed. The mixture was then stirred over 16 hours at 20-25° C., cooled to 5-10° C. over 10 hours and was allowed to stand for over 5 days at SoC. 75 mL of isopropanol was then added over 21 hours, and 100 mL of n-heptane was charged over 12 hours. After filtration and drying, 0.61 g of the sulfate salt of the compound of formula I as crystalline Form I with 98.2% purity was obtained, giving a total 48.8% yield and an epimer A to epimer B ratio of 2.26.

Example 10

4 g of crude sulfate salt of the compound of formula I (BAL0008557-002), HPLC purity 94.9% was dissolved in 200 mL anhydrous ethanol. The pH value was adjusted to 4.5. 0.08 g of crystalline form I was added as seed. The mixture was then stirred over 16 hours at 20-25° C., cooled to 5-10° C. over 10 hours and was allowed to stand for over 5 days at SoC. 150 mL of isopropanol was then added over 18 hours, and 200 mL of n-heptane was charged over 12 hours. After filtration and drying, 1.25 g of the sulfate salt of the compound of formula I as crystalline Form I with 97.4% purity was obtained, giving a total 49.6% yield and an epimer A to epimer B ratio of 1.18.

Example 11

10 g of crude sulfate salt of the compound of formula I (BAL0008557-002), HPLC purity 94.9% was dissolved in 80 mL ethanol and 4 mL water, the pH value was adjusted to 4.4. 0.10 g of crystalline form I was added as seed. The mixture was then stirred over 16 hours at 20-25° C., cooled to 5-10° C. over 10 hours and was allowed to stand for over 6 days at SoC. 200 mL of n-Heptane was then added over 7 hours. The mixture was then stirred over 48 hours at 0-SoC. After filtration and drying, 2.72 g of the sulfate salt of the compound of formula I with 95.8% purity was obtained, giving a total 36.0% yield and an epimer A to epimer B ratio of 0.80.

Example 12

5 g of crude sulfate salt of the compound of formula I (BAL0008557-002), HPLC purity 94.9% was dissolved in 40 mL ethanol and 2 mL water, the pH value was adjusted to 4.4. 0.05 g of crystalline form I was added as seed. The mixture was then stirred over 16 hours at 20-25° C., cooled to 5-10° C. over 10 hours and was allowed to stand for over 6 days at SoC. 100 mL of n-Hexane was then added over 8 hours. The mixture was then stirred over 48 hours at 0-SoC. After filtration and drying, 1.95 g of the sulfate salt of the compound of formula I with 96.6% purity was obtained, giving a total 53.2% yield and an epimer A to epimer B ratio of 1.19.

Example 13

5 g of crude sulfate salt of the compound of formula I (BAL0008557-002), HPLC purity 94.9% was dissolved in 40 mL ethanol and 2 mL water, the pH value was adjusted to 4.4. 0.05 g of crystalline form I was added as seed. The mixture was then stirred over 16 hours at 20-25° C., cooled to 5-10° C. over 10 hours and was allowed to stand for over 6 days at SoC. 100 mL of 1-Hexene was then added over 11 hours. The mixture was then stirred over 48 hours at 0-SoC. After filtration and drying, 1.88 g of the sulfate salt of the compound of formula I with 96.9% purity was obtained, giving a total 51.5% yield and an epimer A to epimer B ratio of 1.20.

Example 14

5 g of crude sulfate salt of the compound of formula I (BAL0008557-002), HPLC purity 94.9% was dissolved in 40 mL ethanol and 2 mL water, the pH value was adjusted to 4.2. 0.05 g of crystalline form I was added as seed. The mixture was then stirred over 16 hours at 20-25° C., cooled to 5-10° C. over 10 hours and was allowed to stand for over 6 days at SoC. 75 mL of isopropanol was then added over 8 hours, 20 mL of n-heptane was then added over 4 hours. The mixture was then stirred over 48 hours at 0-SoC. After filtration and drying, 1.92 g of the sulfate salt of the compound of formula I with 97.8% purity was obtained, giving a total 55.7% yield and an epimer A to epimer B ratio of 1.89.

Example 15

5 g of crude sulfate salt of the compound of formula I (BAL0008557-002), HPLC purity 94.9% was dissolved in 40 mL ethanol and 2 mL water, the pH value was adjusted to 4.2. 0.05 g of crystalline form I was added as seed. The mixture was then stirred over 16 hours at 20-25° C., cooled to 5-10° C. over 10 hours and was allowed to stand for over 6 days at SoC. 20 mL of n-heptane was then added over 4 hours. The mixture was then stirred over 48 hours at 0-SoC. After filtration and drying, 1.30 g of the sulfate salt of the compound of formula I with 97.6% purity was obtained, giving a total 37.1% yield and an epimer A to epimer B ratio of 2.59.

Example 16: Preparation of Crude Sulfate Salt of the Compound of Formula I 13 g of the crude sulfate salt of the compound of formula I (93% area HPLC purity) was dissolved in a mixture of 45 mL ethanol and 5 mL water, the pH value was 2.3. The solution was cooled to −20° C. and left to stand in a refrigerator for 14 days for recrystallization. After filtration and drying, 5 g of the sulfate salt of the compound of formula I as crystalline Form I with 97.8% area HPLC purity was obtained in 41% yield (Epimer ratio not determined).

Example 17: Separation of the Epimers of the Sulfate Salt of the Compound of Formula I The HPLC column used was a Shiseido Chiral CD-Ph 5 µm column with dimensions 250 mm×4.6 mm. The HPLC detector wavelength was 290 nm and the column was maintained at a temperature of 40° C.±5° C. The HPLC samples were prepared by dissolving 10 mg of product in 50 mL of dissolution mixture containing water, acetonitrile and trifluoroacetic acid in proportions 100:100:0.1, which was shaken to homogenize the mixture. The HPLC mobile phase was a mixture of triethylammonium acetate and acetonitrile in proportions 40:60, pH 6.5. The mixture was shaken to homogenize and degassed. The injection volume was 10 µL and the flow rate was 1 mL/minute.

The retention times of the epimers were as follows:
Epimer A: 80 minutes
Epimer B: 84 minutes

Example 18: Characterisation of Form I and Form II of the Sulfate Salt of the Compound of Formula I XRPD patterns were obtained using a high-throughput XRPD set-up. The plates were mounted on a Bruker GADDS diffractometer equipped with a Hi-Star area detector. The XRPD platform was calibrated using Silver Behenate for the long d-spacings and Corundum for the short d-spacings. Data collection was carried out at room temperature using monochromatic CuKα, radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90 seconds for each frame. No background subtraction or curve smoothing was applied to the XRPD patterns. The carrier material used during XRPD analysis was transparent to X-rays and contributed only slightly to the background.

Figure 1:
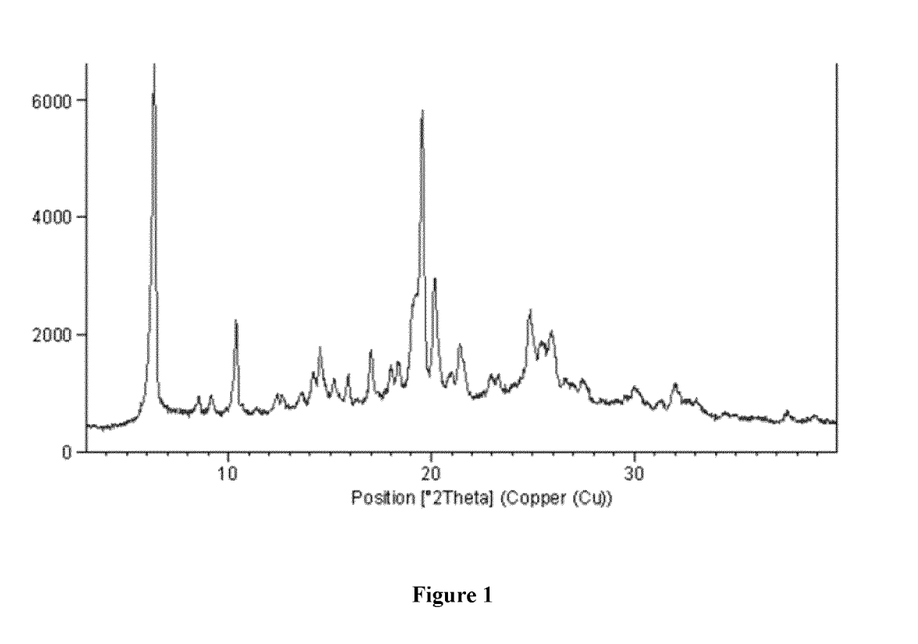
FIG. 1 shows an XRPD diffractogram of Form I of the sulfate salt of the compound of formula I.
Figure 2:
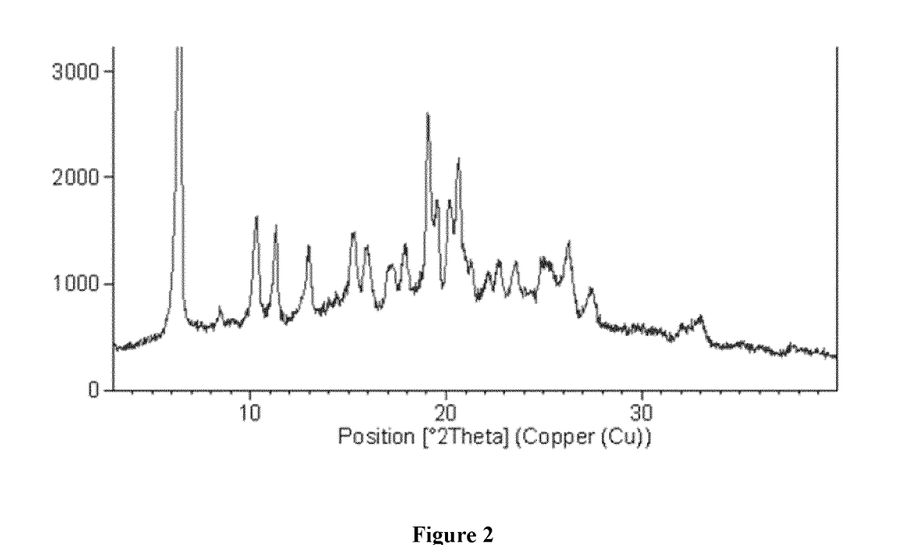
FIG. 2 shows an XRPD diffractogram of Form II of the sulfate salt of the compound of formula I.

The XRPD of Form I at room temperature is shown in FIG. 1 and its diffractogram peaks are shown in Table 1. The XRPD of Form II at room temperature is shown in FIG. 2 and its diffractogram peaks are shown in Table 2.

TABLE 1

List of XRPD peak position of Form I

| Angle [2θ] | d-Spacing [Å] | Intensity [rel %] |
|---|---|---|
| 6.37 | 13.87 | 100.00 |
| 10.38 | 8.52 | 27.60 |
| 14.52 | 6.10 | 19.42 |
| 17.02 | 5.21 | 18.64 |
| 19.04 | 4.66 | 28.44 |
| 19.55 | 4.54 | 80.98 |
| 20.18 | 4.40 | 38.04 |
| 21.41 | 4.15 | 20.34 |
| 24.81 | 3.59 | 27.73 |
| 25.98 | 3.43 | 22.51 |

TABLE 2

List of XRPD peak position of Form I

| Angle [2θ] | d-Spacing [Å] | Intensity [rel %] |
|---|---|---|
| 6.29 | 14.04 | 100.00 |
| 6.51 | 13.57 | 94.26 |
| 10.33 | 8.57 | 42.08 |
| 11.31 | 7.82 | 38.34 |
| 12.96 | 6.83 | 30.89 |
| 15.16 | 5.85 | 31.56 |
| 19.07 | 4.65 | 76.34 |
| 19.57 | 4.53 | 45.68 |
| 20.12 | 4.41 | 44.40 |
| 20.67 | 4.30 | 59.27 |

Comparative Example 1 (CN106565699)

5 g of the crude sulfate salt of the compound of formula I was dissolved in 50 mL water and the solution was treated with saturated sodium bicarbonate at 0° C. to adjust the pH to 7. Then the solution was extracted with 50 mL methylene chloride and the organic phase was concentrated to dryness. The crude product was dissolved in 10 mL of methanol at −5° C. and then the solution was treated with 6.7 g sulfuric acid and 8.3 g 30% aqueous hydrogen peroxide for 30 min, after concentration to dryness. The product decomposed dramatically and no crystalline solid formed.

Comparative Example 2 (CN106467534)

In a 250 mL flask, 62 mL of acetone, 2.65 mL of pure water and 5 mL of 2-Methoxyethanol were added. 5 g of the crude sulfate salt of the compound of formula I with HPLC purity 97.2% with an epimer A to epimer B ratio of 1:1 was added. The solution was stirred at 0-10° C. for 1 hour, then 41 mL of ethyl acetate was added dropwise and the solution was stirred for 10 hours at 0-5° C. The mixture was filtered under nitrogen and the cake was dried for 30 minutes to give 4 g of the sulfate salt of the compound of formula I as crystalline Form I with 98.9% HPLC purity and with 71.6% yield. The epimer ratio of epimer A to epimer B was 1:16.

Comparative Example 3 (CN106467534)

In a 250 mL flask, 62 mL of acetone, 2.65 mL of pure water and 5 mL of 2-Methoxyethanol were added. 5 g of the crude sulfate salt of the compound of formula I with 92.8% HPLC purity 92.8% with an epimer A to epimer B ratio of 3.2:1 was then added. The solution was stirred at 0-10° C. for 1 hour and then 41 mL of ethyl acetate was added dropwise and the solution was stirred for 10 hours at 0-5° C. The mixture was filtered under nitrogen and the cake was dried for 30 minutes to give 0.7 g of the sulfate salt of the compound of formula I as crystalline Form I with 96.3% HPLC purity with 13% yield. The epimer ratio of epimer A to epimer B was 1:2.

The invention claimed is:

1. A method for purifying the sulfate salt of the compound of formula I:

(I)

comprising the steps of:
(a) providing a mixture comprising the sulfate salt of the compound of formula I and an aliphatic alcohol, wherein the pH of the mixture is in the range of about pH 1 to about pH 6;
(b) allowing a first portion of the sulfate salt of the compound of formula I to crystalize from the mixture; and
(c) adding an aprotic organic solvent to the mixture and allowing an additional portion of the sulfate salt of the compound of formula I to precipitate from the mixture; wherein the aprotic organic solvent is C4-C10alkyl, or C4-C10alkenyl or a mixture thereof.

2. The method according to claim 1, wherein the molar ratio of the epimers in the combined portions of the sulfate salt of the compound of formula I from step (b) and step (c) taken together is in the range of 1:2 to 2:1.

3. The method according to claim 1, wherein the aliphatic alcohol is C2-C10alkyl-OH or C3-C10cycloalkyl-OH or a mixture thereof.

4. The method according to claim 3, wherein the aliphatic alcohol is ethanol, propanol, butanol or pentanol or a mixture thereof.

5. The method according to claim 4, wherein the aliphatic alcohol is ethanol.

6. The method according to claim 1, wherein the v/w ratio of the aliphatic alcohol to the sulfate salt of the compound of formula I is in the range of 2:1 to 6:1.

7. The method according to claim 1, wherein the mixture in step (a) comprises the sulfate salt of the compound of formula I, an aliphatic alcohol and water.

8. The method according to claim 7, wherein the v/v ratio of the aliphatic alcohol to water is in the range of 5:1 to 50:1.

9. The method according to claim 1, wherein the pH of the mixture in step (a) is in the range of about pH 3 to about pH 5.

10. The method according to claim 9, wherein the pH of the mixture in step (a) is in the range of about pH 3.8 to about pH 4.5.

11. The method according to claim 1, wherein step (b) comprises cooling the mixture and wherein the rate of cooling is not more than 3° C. per hour.

12. The method according to claim 1, wherein the aprotic organic solvent is hexene, heptene, hexane or heptane or a mixture thereof.

13. The method according to claim 12, wherein the aprotic organic solvent is n-heptane.

14. The method according to claim 1, wherein the volume of aprotic organic solvent used in step (c) is in the range of 0.05 to 8 times the volume of the mixture in step (a).

15. The method according to claim 1, wherein the method comprises
(a) providing a mixture comprising the sulfate salt of the compound of formula I and ethanol and optionally water, wherein the pH of the mixture is in the range of about pH 1 to about pH 6;
(b) allowing a first portion of the sulfate salt of the compound of formula I to crystalize from the mixture;
(c1) adding propanol and/or butanol to the mixture and allowing an additional portion of the sulfate salt of the compound of formula I to precipitate from the mixture; and
(c2) adding hexane or heptane or a mixture thereof to the mixture and allowing a further additional portion of the sulfate salt of the compound of formula I to precipitate from the mixture.

16. The method according to claim 1, comprising the steps of
(a) providing a mixture comprising the sulfate salt of the compound of formula I and an aliphatic alcohol, wherein the aliphatic alcohol is C2-C10alkyl-OH or C3-C10cycloalkyl-OH or a mixture thereof, wherein the v/w ratio of the aliphatic alcohol to the sulfate salt of the compound of formula I is in the range of 1:1 to 100:1, and wherein the pH of the mixture is in the range of about pH 3 to about pH 5;
(b) allowing a first portion of the sulfate salt of the compound of formula I to crystalize from the mixture; and
(c) adding an aprotic organic solvent to the mixture, wherein the aprotic organic solvent is C4-C10alkyl, or C4-C10alkenyl or a mixture thereof, wherein the volume of aprotic organic solvent used in step (c) is in the range of 0.05 to 8 times the volume of the mixture in step (a), and allowing an additional portion of the sulfate salt of the compound of formula I to precipitate from the mixture.

17. The method according to claim 1, comprising the steps of
   (a) providing a mixture comprising the sulfate salt of the compound of formula I, water and ethanol, wherein the v/w ratio of the ethanol to the sulfate salt of the compound of formula I is in the range of 2:1 to 6:1, wherein the v/v ratio of ethanol to water is 15:1 to 25:1, and wherein the pH of the mixture is in the range of about pH 3 to about pH 5;
   (b) cooling the mixture and allowing a first portion of the sulfate salt of the compound of formula I to crystalize from the mixture, wherein the rate of cooling is not more than 3° C. per hour;
   (c1) adding propanol and/or butanol to the mixture, wherein the volume of propanol and/or butanol is 1 to 6 times the volume of the mixture in step (a) and allowing an additional portion of the sulfate salt of the compound of formula I to precipitate from the mixture; and
   (c2) adding an aprotic organic solvent to the mixture, wherein the aprotic organic solvent is hexane or heptane or a mixture thereof, wherein the volume of aprotic organic solvent is in the range of 1 to 6 times the volume of the mixture in step (a), and allowing a further additional portion of the sulfate salt of the compound of formula I to precipitate from the mixture;
and wherein the molar ratio of the epimers in the combined portions of the sulfate salt of the compound of formula I from step (b) and steps (c1) and (c2) taken together is in the range of 1:2 to 2:1.

18. A method for preparing epimer A of the sulfate salt of the compound of formula I as defined in claim 1 in solid form, wherein epimer A is the first epimer of the epimers to elute from a chiral HPLC column functionalized with phenylcarbamated β-cyclodextrin in which the mobile phase is a mixture of triethylammonium acetate and acetonitrile in proportions 40:60 at pH 6.5, comprising the step of
   (c) adding an aprotic organic solvent to a mixture comprising the sulfate salt of epimer A and an aliphatic alcohol, wherein the pH of the mixture is in the range of about pH 1 to about pH 6; and allowing the sulfate salt of epimer A to precipitate from the mixture; wherein the molar amount of epimer A in the precipitate from step (c) is greater than the molar amount of epimer B present in the precipitate from step (c);
   wherein the aprotic organic solvent is C4-C10alkyl or C4-C10alkenyl or a mixture thereof.

19. The method according to claim 18, wherein the aliphatic alcohol contains one or two OH groups, providing that when there are two OH groups there are three to six carbon atoms in the aliphatic moiety, and wherein the aliphatic moiety is a non-aromatic hydrocarbon moiety in which the constituent carbon atoms can be straight-chain, branched chain or cyclic.

20. The method according to claim 18, wherein the term "about" indicates a variation of +/−5% of the given value.

21. A method for preparing a pharmaceutical composition comprising the sulfate salt of the compound of formula I as defined in claim 1 the method comprising (i) purifying the sulfate salt of the compound of formula I by the method as defined in claim 1 and (ii) formulating the sulfate salt of the compound of formula I with one or more pharmaceutical excipients.

22. A pharmaceutical composition comprising the sulfate salt of the compound of formula I as defined in claim 1 and one or more pharmaceutical excipients, wherein the sulfate salt of the compound of formula I has been purified by a method as defined in claim 1.

23. The method according to claim 1, wherein the aliphatic alcohol contains one or two OH groups, providing that when there are two OH groups there are three to six carbon atoms in the aliphatic moiety, and wherein the aliphatic moiety is a non-aromatic hydrocarbon moiety in which the constituent carbon atoms can be straight-chain, branched chain or cyclic.

24. The method according to claim 1, wherein the mixture provided in step (a) comprises a mixture of the epimers of the sulfate salt of the compound of formula I, wherein epimer A is the first epimer and epimer B is the second epimer to elute from a chiral HPLC column functionalized with phenylcarbamated β-cyclodextrin in which the mobile phase is a mixture of triethylammonium acetate and acetonitrile in proportions 40:60 at pH 6.5; and wherein the molar ratio of epimer B to epimer A in the portion of the sulfate salt of the compound of formula I obtained from step (b) is greater than 1:1.

26. The method according to claim 1, wherein the mixture provided in step (a) comprises a mixture of the epimers of the sulfate salt of the compound of formula I, wherein epimer A is the first epimer and epimer B is the second epimer to elute from a chiral HPLC column functionalized with phenylcarbamated β-cyclodextrin in which the mobile phase is a mixture of triethylammonium acetate and acetonitrile in proportions 40:60 at pH 6.5; and wherein step (b) selectively crystallizes epimer B and step (c) is effective for precipitating epimer A remaining in solution.

25. The method according to claim 1, wherein the mixture provided in step (a) comprises a mixture of the epimers of the sulfate salt of the compound of formula I, wherein epimer A is the first epimer and epimer B is the second epimer to elute from a chiral HPLC column functionalized with phenylcarbamated β-cyclodextrin in which the mobile phase is a mixture of triethylammonium acetate and acetonitrile in proportions 40:60 at pH 6.5; and wherein the molar ratio of epimer A to epimer B in the portion of the sulfate salt of the compound of formula I obtained from step (c) is greater than 1:1.

27. The method according to claim 1, wherein step (b) comprises allowing crystallization by cooling the mixture and allowing the mixture to stand for a suitable period.

28. The method according to claim 1, wherein the term "about" indicates a variation of +/−5% of the given value.

29. The method according to claim 1, comprising the steps of:
(a) providing a mixture comprising the sulfate salt of the compound of formula I and an aliphatic alcohol, wherein the pH of the mixture is in the range of about pH 1 to about pH 6;
(b) allowing a first portion of the sulfate salt of the compound of formula I to crystalize from the mixture by cooling the mixture and allowing the mixture to stand for a suitable period; and
(c) adding an aprotic organic solvent to the mixture and allowing an additional portion of the sulfate salt of the compound of formula I to precipitate from the mixture;
wherein the aliphatic alcohol is ethanol, propanol, butanol, pentanol, cyclopentanol, cyclohexanol, or a mixture thereof;
wherein the aprotic organic solvent is C4-C10alkyl, or C4-C10alkenyl or a mixture thereof;
wherein the term "about" indicates a variation of +/−5% of the given value.

* * * * *